United States Patent [19]

Driscoll et al.

[11] Patent Number: 4,842,697
[45] Date of Patent: Jun. 27, 1989

[54] METHOD OF DETERMINING AMMONIA IN A GASEOUS OR LIQUID SAMPLE

[75] Inventors: John N. Driscoll, Wellesley Hills; Edwards S. Atwood, Natick, both of Mass.

[73] Assignee: HNU Systems, Inc., Newton, Mass.

[21] Appl. No.: 245,466

[22] Filed: Sep. 16, 1988

Related U.S. Application Data

[60] Division of Ser. No. 38,849, Apr. 15, 1987, Pat. No. 4,780,185, which is a division of Ser. No. 810,412, Dec. 18, 1985, Pat. No. 4,659,434, which is a division of Ser. No. 726,957, Aug. 26, 1985, abandoned, which is a continuation of Ser. No. 526,914, Aug. 26, 1983, abandoned.

[51] Int. Cl.$^4$ .................. G01N 27/30; G01N 27/56
[52] U.S. Cl. ....................... 204/1 T; 204/415
[58] Field of Search ................. 204/415, 1 N

[56]  References Cited

U.S. PATENT DOCUMENTS

| | | | |
|---|---|---|---|
| 3,649,505 | 3/1972 | Strickler et al. | 204/195 |
| 3,756,923 | 9/1973 | Dahms | 204/1 T X |
| 3,763,025 | 10/1973 | Chand | 204/1 T |
| 3,795,589 | 3/1974 | Dahms | 204/1 T |
| 3,803,006 | 4/1974 | Krueger et al. | 204/1 |
| 3,830,709 | 8/1974 | Krueger et al. | 204/1 T |
| 3,830,718 | 8/1974 | Riseman et al. | 204/195 |
| 3,859,191 | 1/1975 | Frant et al. | 204/195 |
| 3,897,315 | 7/1975 | Riseman et al. | 204/1 |
| 4,092,232 | 5/1978 | Zetter | 204/415 |
| 4,105,525 | 8/1978 | Synott et al. | 204/195 |
| 4,197,853 | 4/1980 | Parker | 128/635 |
| 4,474,648 | 10/1984 | Tantram et al. | 204/1 T |

Primary Examiner—G. L. Kaplan

[57] ABSTRACT

A method of determining ammonia in a gaseous or liquid sample is disclosed. A sensor comprising a sensing electrode, a reference electrode, a semi-permeable membrane and an electrolyte is used. The electrolyte is buffered to a pH value between 4.5 and 6.5 and is initially free of any salt capable of dissociating to form therein ammonium ion. The electrolyte may optionally contain at least 25% v/v of a water miscible solvent having a dielectric constant of at least 10. In the latter case the pH of the electrolyte is between 5.5 and 7.5. The potential between the sensing electrode and reference electrode is monitored as a measure of ammonia in the sample.

4 Claims, 1 Drawing Sheet

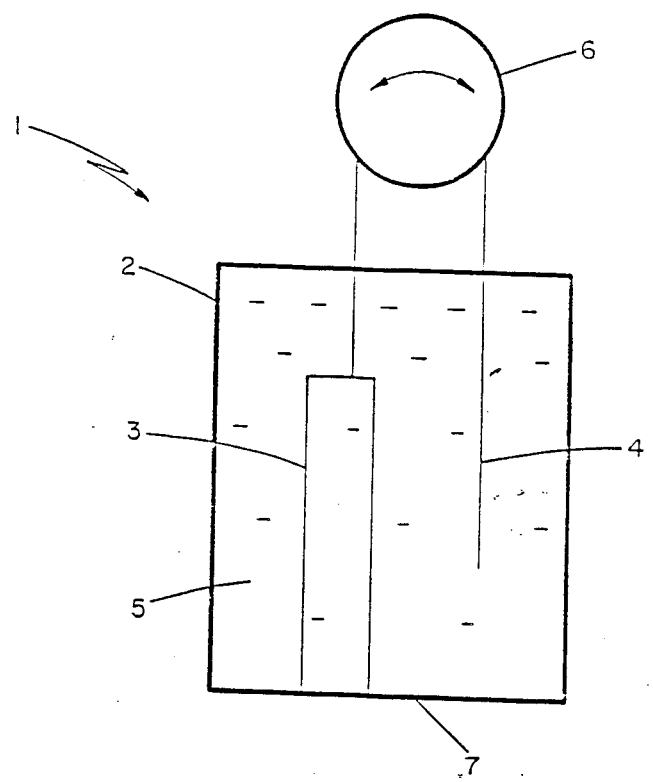

METHOD OF DETERMINING AMMONIA IN A GASEOUS OR LIQUID SAMPLE

BACKGROUND OF THE INVENTION

This application is a division of Ser. No. 038,849, filed Apr. 15, 1987, now U.S. Pat. No. 4,780,185, which in turn was a division of Ser. No. 810,412, filed Dec. 18, 1985, now U.S. Pat. No. 4,659,434, which in turn was a division of Ser. No. 726,957, filed Aug. 26, 1985, now abandoned, which in turn was a continuation of Ser. No. 526,914, filed Aug. 26, 1983, now abandoned.

This invention relates to electrochemical analysis and more particularly to gas detection electrochemical cells.

Gas detection electrochemical cells are known in which a detection electrode is arranged in a body containing an electrolyte. A gas permeable membrane is provided to separate the electrode and electrolyte from the sample and to permit passage of gas to a film of electrolyte, between the membrane and the electrode, which connects the detection electrode to a reference electrode.

A number of different gases have been measured using such systems, and a variety of electrolytes have been employed. Frant et al. U.S. Pat. No. 3,859,191 describes an HCN-sensing electrochemical cell employing an electrolyte containing $KAg(CN)_2$. Riseman et al. U.S. Pat. No. 3,897,315 describes an $H_2S$-sensing electrochemical cell employing an ion-specific reference electrode. Kureger et al. U.S. Pat. No. 3,803,006 describes an $SO_2$-sensing electrochemical cell employing an electrolyte containing $Na_2SO_3$. Strickler et al. U.S. Pat. No. 3,649,505 describes an $NH_3$-sensing electrochemical cell employing an electrolyte containing $NH_4Cl$. Riseman et al. U.S. Pat. No. 3,830,718 describes an $NH_3$-sensing electrochemical cell employing an electrolyte containing ammonium picrate. Synnott et al. U.S. Pat. No. 4,105,525 describes an $NH_3$-sensing electrochemical cell employing an electrolyte containing 5,5'-Nitrilodibarbituric acid ammonium salt.

The present invention provides improved electrochemical cells for detecting any of a variety of chemical gases.

In general the invention features, in a first aspect, an electrochemical cell for detecting, in a gaseous or liquid sample, any of the gases $SO_2$, $NO_x$ (nitrogen oxide), HNC, $NH_3$, formic acid, acetic acid, or $C_2$. The cell includes a body and within the body a detection electrode, a reference electrode, a liquid electrolyte connecting the electrodes, and a membrane permeable to the gas in close proximity to the detection electrode and arranged to separate the electrodes and the electrolyte from the sample. The electrolyte is buffered to a pH value such that the electrochemical cell gives a slope of response to the gas within 25% of a Nernstian response. (As is well known, a Nernstian response is a change in measured potential, with a ten-fold change in concentration, which ideally fits the Nernst equation. For a monovalent ion, the potential change is 59.16 mv at 25° C.; a response within 25% of this is between 44.37 and 73.95 mv). The electrolyte is initially (prior to use) essentially (over 99%, v/v) free of any salt capable of dissociating to form in said electrolyte a weak acid or weak base (other than $H_3O^+$ or $OH^-$) which forms upon dissociation of the gas being measured. The reference electrode in contact with the electrolyte is operative at the pH value of the liquid electrolyte.

In preferred embodiments of the above first aspect of the invention, the liquid electrolyte is an aqueous buffer solution containing, at a concentration of between 0.5% and 70%, v/v, a water-miscible solvent having a dielectric constant of at lest 10 and being non-interfering with the detection and reference electrodes.

In other preferred embodiments of the above first aspect of the invention, the detection electrode is a pH electrode or an ion-specific electrode selective for an ionic species formed in the electrolyte upon dissociation of the gas therein; and the reference electrode is a silver-based electrode, a platinum-based electrode, or an ion selective electrode the primary electrode of which is in contact with the electrolyte which electrolyte contains the ionic species for which the ion-specific reference electrode is selective. The reference electrode is selected so that the ionic species for which it is selective is substantially (over 90%) uncomplexed at the pH of the electrolyte.

In a second aspect the invention features, in general, an electrochemical cell for detecting $H_2S$ in a gaseous or liquid sample, the cell including a body and within the body a detection electrode, a reference electrode which is not an ion selective electrode, a liquid electrolyte connecting the electrodes, and a membrane permeable to $H_2S$ in close proximity to the detection electrode and arranged to separate the electrodes and the electrolyte from the sample. The liquid electrolyte is an aqueous buffer solution buffered to a pH value such that the electrochemical cell gives a slope of response to the $H_2S$ within 25% of a Nernstian response. The reference electrode in contact with the electrolyte is operative at the pH value of the liquid electrolyte.

In preferred embodiments of the above second aspect of the invention, the liquid electrolyte contains a water-miscible solvent having a dielectric constant of at least 10 and being non-interfering with the detection and reference electrodes; the solvent is present in a concentration of at least 25%, v/v,; the detection electrode is a pH electrode or sulfide ion selective electrode; the reference electrode is a silver-based electrode or a platinum-based electrode; the reference electrode is selected so that the ionic species to which it responds is substantially (over 90%) uncomplexed at the pH of the electrolyte; and the electrolyte is initially (prior to use) essentially (over 99%, v/v) free of any salt capable of dissociating in the electrolyte to form $HS^-$.

We have discovered realtionships in the above systems betweeen the pK of the gas being detected and the optimum pH of the liquid electrolyte. One relationship is similar for all of the protonated gases, and another is similar for all of the non-protonated gases. Consequently, in preferred embodiments of all of the above aspects of the invention, where the gas being detected is one of the protonated gases $H_2S$, HCN, formic acid, or acetic acid, the pH of the liquid electrolyte is within 2.3 units of the pK of the gas, most preferably within 1.0 unit of the pK of the gas.

Where the gas being detected is one of the non-protonated gases $SO_2$, $NH_3$, $NO_x$, or $CO_2$, the pH of the liquid electrolyte is at least 1.7 units above or below the pK of the gas, most preferably at least 2.7 units above or below the pK of the gas.

The electrochemical cells of the invention have the advantages of stability and economy. For example, the $SO_2$ electrode is, as far as is known, the first commercially practical device, prior devices having contained salts, dissociating to form $HSO_3^-$ or $SO_3^{-,-}$, which were extremely unstable and tended to decompose during storage. Furthermore, where the electrolyte is essentially free of any salt capable of dissociating to form the weak acid or weak base which forms upon dissociation of the gas being measured, an ion selective electrode can be used as the detection electrode, an option not available when the electrolyte already contains the ion to be measured. This advantage can be particularly important in situations in which two gases with close pK values are likely to be present in one sample, so that a pH change observed using a pH electrode as the detection electrode could be attributed to either of the gases, and an ion selective detection electrode must therefore be used to give an accurate result. A further advantage is that the absence of such a salt can in some cases (e.g. in the case of HCN detection) allow the avoidance of toxic or corrosive substances.

Other objects, features, and advantages of this invention will be apparent to those skilled in the art from the following detailed description of preferred embodiments thereof taken together with the accompanying drawing, in which:

The FIGURE is a diagrammatic representation of an electrochemical cell embodying the invention.

Referring to the FIGURE, the diagrammatic electrochemical cell, generally designated 1, comprises body 2, detection electrode 3, reference electrode 4, output measuring device 6, liquid electrolyte 5, and selectively permeable surface 7 across which the gas to be detected passes. Detection electrode 3 can be a pH electrode or an ion selective electrode which is selective for an ionic species which forms in the electrolyte upon dissociation of the gas being detected. For example, ion selective detection electrodes advantageously can be used, in accordance with the invention, to measure $H_2S$, HCN, and $CO_2$. HCN can be measured, for example, using an electrode containing a membrane composed of $Ag_3AsS_3$ and silver cyanide, as disclosed in copending patent application Ser. No. 496,113, filed May 19, 1983, assigned to the same assignee as the present invention, hereby incorporated by reference.

For measuring gases other than $H_2S$, the reference electrode 4 can also be an ion selective electrode which is operative at the pH of the electrolyte. In such case, the electrolyte will contain an ion for which the reference electrode can respond. An example of an ion selective reference electrode suitable for use with the subject gases is a sodium ion selective electrode; its use requires the presence in the electrolyte of sodium ions, which can be provided by any suitable salt, e.g., NaCl.

The liquid electrolytes of the invention can be used in conjunction with commercially available gas detecting electrochemical cells, e.g., the Series 10 electrochemical cells having a pH detection electrode and an Ag/AgCl reference electrode made by NHU Systems, Inc., Newton, Mass., as well as in electrochemical cells employing ion selective detection electrodes, as described above.

The composition of the electrolyte is dependent on the gas to be detected. Generally, the electrolyte contains an inert buffer and a dissociated salt for providing an ion to which the reference electrode can respond. Optionally the electrolyte also contains up to 70%, v/v, of a water-miscible solvent having a dielectric constant of at least 10 (dielectric constant is a measure of polarity, a necessary property of the solvent) and is essentially free of salts of the weak acid or weak base, other than $H_3O^+$ or $OH^-$, formed upon dissociation of the gas being measured.

The pH of the electrolyte is preferably such that the slope of the response of the electrochemical cell is within 25% of Nernstian. The pH also bears a relationship to the pK of the gas, as discussed above; the relationship depends on whether or not the gas is protonated.

The other electrode characteristics, in addition to slope, which vary with electrolyte composition are speed of response, lower limit of detection, and stability of response (minimization of drift). Since an electrolyte composition which optimizes one electrode characteristic may not optimize others, the composition will normally be tailored to optimize whatever characteristic is most important for a given application while keeping the other characteristics within acceptable limits, and while ensuring that the slope is never farther than 25% from Nernstian.

The starting point for the preparation of an electrolyte for a given application generally is to porepare an inert aqueous buffer solution (e.g. phosphate or borate) which has a 0.01M concentration of a salt capable of dissociating to form an ion to which the refrence electrode can respond (for example, NaCl if the reference electrode is Ag/AgCl; NaF if the reference electrode is an ion selective fluoride electrode). A water-miscible, non-interfering solvent having a dielectric constant of at least 10 may then be added, if desired, in a concentration of 0.5%, v/v. The pH of multiple samples of the electrolyte is then varied, beginning with a pH value within 2.3 units of the pK of the gas being detected, if the gas is protonated, or more than 1.7 units higher or lower than the gas being detected if it is not protonated (the pH of the electrolyte is lower than the pK in the case of the alkaline gas $NH_3$, and higher in the case of the other non-protonated gases).

Each sample is then tested in an electrochemical cell and the four electrode characteristics discussed above are measured. The pH corresponding to the best performance is then held constant and the composition of the electrode is then varied in terms of salt and solvent concentration to further optimize electrode characteristics.

The water-miscible solvent is an optional ingredient when gas measurement is carried out in a liquid in contact with the gas permeable membrane of the electrochemical cell. When measurement is carried out in the headspace between the membrane and a liquid sample, or in the atmosphere, or when the gas being measured is $SO_2$, it is preferable that the electrolyte contain a water-miscible solvent.

The reason the solvent is desirable when the membrane is not in contact with a liquid sample is that, without the solvent, water tends to move in and out of the solution, causing continual drifting of response. The solvent minimizes such movement of water and this stabilizes response. when the gas is to be measured in the headspace or the atmosphere, the solvent is preferably present in a concentration of at least 25%, v/v, and in some instances can be as high as 70%, v/v. Generally, the optimal pH of the electrolyte will increase with an increasing solvent concentration.

The optimal pH of the electrolyte will vary not only with solvent concentration, but with solvent polarity as well. Generally, more polar sovents require a larger upward adjustment of pH than less polar solvents.

Any inert, water-miscible solvent of sufficient polarity can be used. Most commonly the solvent is a suitable monohydroxylic alcohol, diol, or polyol. Examples of useful alcohols are 2-methyoxy ethanol, diethylene glycol, glycerol, and propylene glycol. Non-alcoholic solvents, e.g. dimethyl sulfoxide, can also be used.

The buffer employed in the electrolyte can be any suitable inert (non-interfering) buffer, e.g. phosphate, borate, formate, citrate, acetate, or Tris.

The reference electrode, as well as being of one of the types mentioned above, can alternatively be a redox potential electrode, e.g. a platinum electrode, which does not require the presence in the electrolyte of any particular ion; a stable concentration of any electrolyte is sufficient.

The table below shows preferred pH values and preferred pH ranges of electrolytes useful for measuring various gases. The table gives pH ranges and values for electrolytes containing high and low water-miscible solvent concentrations. The table also gives preferred electrolyte compositions. In each case, the detection electrode is assumed to be a pH electrode and the reference electrode either platinum or Ag/AgCl. Each electrolyte, when used to measure the corresponding listed gas, gives a slope within 25% of Nernstian.

Other embodiments of this invention will occur to those skilled in the art which are within the scope of the following claims.

What is claimed is:

1. A method for detecting $NH_3$ in a gaseous or liquid sample, said method comprising testing said sample in an electrochemical cell comprising a body and within said body a detection electrode, a reference electrode, a liquid electrolyte connecting said electrodes, and a membrane permeable to said gas in close proximity to said detection electrode and arranged to separate said electrodes and said electrolyte from said sample, said liquid electrolyte being an aqueous buffer solution buffered to a pH value of between 5.5 and 7.5 and being initially essentially free of any salt capable of dissociating to form in said electrolyte $NH_4^+$, said electrolyte containing at least 25% v/v of a water miscible solvent having a dielectric constant of at least 10 and being non-interfering with said detecting and reference electrodes.

2. The method of claim 1 wherein said testing comprises measuring a change in potential between said reference electrode and said detection electrode.

3. A method for detecting $NH_3$ in a gaseous or liquid sample, said method comprising testing said sample in

| Gas | Weak Acid Or Weak Base | pK | Preferred pH Range; No Solvent | Preferred pH Range; at Least 25% Solvent | Preferred pH; Less Than 1% Solvent | Preferred pH; 35% Solvent | Preferred Electrolyte Compositions Low Solvent | High Solvent |
|---|---|---|---|---|---|---|---|---|
| $SO_2$ | $HSO_3^-$ or $SO_3^-$ | 1.8 | 4.8–6.0 | 6.0–7.2 | 5.25 | 6.5 | 0.025 M Phosphate Buffer pH 5.25 0.010 M NaCl 0.5% (v/v) Ethylene Glycol | 0.05 M Phosphate Buffer pH 6.5 0.01 M NaCl 35% (v/v) Ethylene Glycol or 0.05 M Phosphate Buffer; pH 6.5 0.01 M NaCl 45% (v/v) Ethylene Glycol |
| $H_2S$ | $HS^-$ | 7.0 | 6.3–7.8 | 7.3–8.8 | 7.0 | 8.0 | .05 M Phosphate Buffer; pH 7.0 .01 M NaCl 0.5% (v/v) Ethylene Glycol | 0.05 M Borate Buffer; pH 8.0 0.01 M NaCl 35% Ethylene Glycol |
| HCN | $Cl^-$ | 9.3 | 8.3–9.8 | 9.5–11.6 | 9.0 | 10.0 | 0.1 M Borate Buffer; pH 9.0 0.01 M NaCl | 0.1 M Borate Buffer pH 10.0; .01 M NaCl 35% Ethylene Glycol |
| $NH_3$ | $NH_4^+$ | 9.2 | 4.5–6.5 | 5.5–7.5 | 5.5 | 6.5 | .01 M Phosphate Buffer; pH 5.5 .01 M NaCl; .5% ethylene glycol | .01 M Phosphate Buffer; pH 6.5 .01 M NaCl; 65% Ethylene Glycol |
| $NO_x$ | $NO_2^-$ | 3.4 | 6.8–8.0 | 8.0–9.2 | 7.25 | 6.5 | .05 M Phosphate Buffer; pH 7.25 0.01 M NaCl 0.5% (v/v) Ethylene Glycol | .01 M Phosphate Buffer; pH 8.5 .01 M NaCl 35% (v/v) Ethylene Glycol |
| Formic Acid | $HCO_2^-$ | 3.8 | 2.8–4.3 | 4.0–5.5 | 3.8 | 4.8 | .05 M Phosphate Buffer; pH 3.8 .01 M NaCl 0.5% (v/v) Ethylene Glycol | .05 M Phosphate Buffer; pH 4.8 .01 M NaCl 35% (v/v) Ethylene Glycol |
| Acetic Acid | $CH_3CO_2^-$ | 4.8 | 4.0–5.5 | 5.0–6.5 | 4.8 | 5.8 | .05 M Phosphate Buffer; pH 4.8 .01 M NaCl 0.5% (v/v) Ethylene Glycol | .05 M Phosphate Buffer; pH 5.8 .01 M NaCl 35% (v/v) Ethylene Glycol |
| $CO_2$ | $HCO_3^-$ | 6.4 | 9.5–11.0 | 10.7–12.0 | 9.8 | 11.0 | .01 M Phosphate Buffer; pH 9.8 .01 M NaCl 0.5% (v/v) Ethylene Glycol | .01 M Phosphate Buffer; pH 11.0 .01 M NaCl 35% (v/v) Ethylene Glycol | an electrochemical cell comprising a body and within said body a detection electrode, a reference electrode, a liquid electrolyte connecting said electrodes, and a membrane permeable to said gas in close proximity to said detection electrode and arranged to separate said electrodes and said electrolyte from said sample, said liquid electrolyte being in aqueous buffer solution buffered to a pH value of between 4.5 and 6.5 and being initially essentially free of any salt capable of dissociating to form in said electrolyte $NH_4^+$.

4. The method of claim 3 wherein said testing comprises measuring a change in potential between said reference electrode and said detection electrode.

* * * * *

UNITED STATES PATENT AND TRADEMARK OFFICE
CERTIFICATE OF CORRECTION

PATENT NO. : 4,842,697

DATED : June 27, 1989

INVENTOR(S) : John N. Driscoll and Edwards S. Atwood

It is certified that error appears in the above-identified patent and that said Letters Patent is hereby corrected as shown below:

Column 1, line 32, "Kureger" should be --Krueger--.

Column 1, line 50, "$C_2$" should be --$CO_2$--.

Column 2, line 16, "... the electrolyte which ..." should be --... the electrolyte, which ...--.

Column 3, line 2, "$SO_3$-,-," should be --$SO_3$--,--.

Column 3, line 57, "NHU" should be --HNU--.

Column 4, line 22, "porepare" should be --prepare--.

Column 4, line 59, "when" should be --When--.

Column 2 of the chart entitled "Weak Acid Or Weak Base" requires the following changes:

line 6, "$HSO_3$" should be --$HSO_3^-$--.

line 8, "$SO_3^-$" should be --$SO_3^{--}$--.

UNITED STATES PATENT AND TRADEMARK OFFICE
CERTIFICATE OF CORRECTION

PATENT NO. : 4,842,697

DATED : June 27, 1989

INVENTOR(S) : John N. Driscoll and Edwards S. Atwood

It is certified that error appears in the above-identified patent and that said Letters Patent is hereby corrected as shown below:

line 23, "Cl$^-$" should be --CN$^-$--.

Column 7, line 7, "in" should be --an--.

Signed and Sealed this

Thirteenth Day of April, 1993

Attest:

STEPHEN G. KUNIN

*Attesting Officer*   *Acting Commissioner of Patents and Trademarks*